United States Patent [19]

Witte et al.

[11] 3,997,667
[45] Dec. 14, 1976

[54] 1-[3-(NAPHTH-1-YLOXY)-PROPYL]-PIPERAZINE COMPOUNDS AND THERAPEUTIC COMPOSITIONS

[75] Inventors: Ernst-Christian Witte, Mannheim; Kurt Stach, Mannheim-Waldhof; Max Thiel, Mannheim; Gisbert Sponer, Hemsbach; Egon Roesch, Mannheim, all of Germany

[73] Assignee: Boehringer Mannheim G.m.b.H., Mannheim, Germany

[22] Filed: Jan. 28, 1975

[21] Appl. No.: 544,721

[30] Foreign Application Priority Data
Feb. 23, 1974 Germany .................... 2408803

[52] U.S. Cl. .................. 424/250; 260/268 BC
[51] Int. Cl.$^2$ .................................. C07D 295/08
[58] Field of Search ............ 260/268 PH, 268 BC; 424/250

[56] References Cited
UNITED STATES PATENTS 2,891,063   6/1959   Sommers ............... 260/268 PH
3,270,004   8/1966   Alter ..................... 260/268 PH

OTHER PUBLICATIONS

Cronenberger et al., Chemical Abstracts, vol. 66 (1967) 85761j.

Primary Examiner—Paul M. Coughlan, Jr.
Attorney, Agent, or Firm—Burgess, Dinklage & Sprung

[57] ABSTRACT

New 1-[3-naphth-1-yloxy)-propyl]-piperazine compounds of the formula:

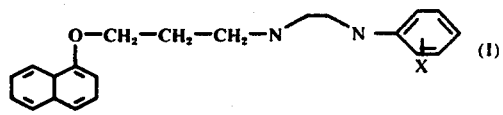

wherein
  X is hydrogen or methoxy;
and the pharmacologically compatible salts thereof; are outstandingly effective in lowering blood pressure and are thus useful as anti-hypertensive agents.

9 Claims, No Drawings

1-[3-(NAPHTH-1-YLOXY)-PROPYL]-PIPERAZINE COMPOUNDS AND THERAPEUTIC COMPOSITIONS

The present invention relates to new 1-[3-(naphth-1-yloxy)-propyl]-piperazine compounds and to therapeutic compositions and uses thereof.

The new 1-[3-(naphth-1-yloxy)-propyl]-piperazine derivatives according to the present invention are compounds of the formula:

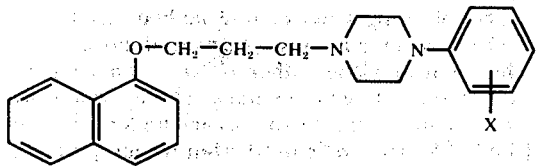

(I)

wherein

X is hydrogen or methoxy;
and the pharmacologically compatible salts thereof.

The new compounds (I) according to the present invention possess outstanding blood pressure-lowering and thus anti-hypertensive properties. Furthermore, they inhibit the anaphylactoid reactions in rats initiated by dextran.

In Chim. Therap., p. 290, 1966, some 1-[3-(naphth-1-yloxy)-propyl]-piperazines are described but without mentioning their pharmacological action. Our investigations have shown that the new compounds (I) according to the present invention surprisingly possess a substantially better anti-hypertensive action than the previously described compounds.

The new compounds according to the present invention can be prepared, for example, by reacting a compound of the formula:

wherein Y and Z, which can be the same or different, are reactive groups, with 1-naphthol and with a piperazine of the formula:

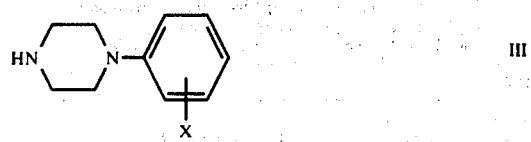

in which X has the same meaning as above, whereafter, if desired, the compound obtained is converted into a pharmacologically compatible salt.

In carrying out this reaction, all three components can be reacted simultaneously. Preferably, however, the reaction is carried out in two stages in which 1-naphthol is first condensed with a compound of formula (II) and the condensation product so formed is then reacted with a compound of formula (III) or compounds of formulae (II) and (III) are first condensed and the product obtained thereafter reacted with 1-naphthol.

These condensation reactions can be carried out in the presence of an acid-binding agent, for example, a tertiary amine (such as triethylamine) or an alkali metal carbonate or bicarbonate, or the sodium or potassium salt of 1-naphthol, which is prepared in known manner, can also be used.

The reaction can be carried out in a solvent, for example a lower ketone (such as methyl ethyl ketone), a lower alcohol (such as isopropanol) or tetrahydrofuran.

The reactive groups Y and Z in the compounds of formula (II) are preferably acid residues, for example residues of hydrohalic or sulfonic acids.

For the preparation of salts, the compounds according to the present invention can be reacted with pharmacologically compatible organic or inorganic acids, for example hydrochloric acid, sulfuric acid, phosphoric acid, lactic acid, citric acid or an alkyl-sulfonic acid.

The following Examples are given for the purpose of illustrating, without limiting, the present invention:

EXAMPLE 1

Preparation of 1-Phenyl-4-[3-(Naphth-1-yloxy)-propyl]-piperazine

A mixture of 14.4 g (0.1 mol) 1-naphthol, 13.8 g (0.1mol) pulverized anhydrous potassium carbonate and 200 ml. anhydrous butan-2-one was heated under reflux for an hour, the reaction mixture was then cooled and 23.9 g (0.1 mol) 1-phenyl-4-(3-chloropropyl)-piperazine added thereto, as well as 0.2 g potassium iodide. The reaction mixture was subsequently maintained at reflux temperature for 24 hours. After cooling, the reaction mixture was filtered with suction, the filtrate was evaporated in a vacuum and the evaporation residue was dissolved in chloroform. The chloroform phase was washed with a dilute aqueous solution of sodium hydroxide and with water, then dried and finally hydrogen chloride passed therethrough. After the addition of ether, there was obtained the dihydrochloride of 1-phenyl-4-[3-(naphth-1-yloxy)-propyl]-piperazine, which was recrystallized from methanol. The yield was 26.8 g (64% of theory); m.p. 220° – 222° C.

In an analogous manner, 1-(2-methoxyphenyl)-4-[3-(naphth-1-yloxy)-propyl]-piperazine was obtained from 1-naphthol and 1-(2-methoxyphenyl)-4-(3-chloropropyl)-piperazine; yield 70% of theory; m.p. of the dihydrochloride 209° – 211° C.

EXAMPLE 2

Preparation of 1-(4-Methoxyphenyl)-4-[3-(naphth-1-yloxy)-propyl]-piperazine 152 g (1.1 mol) pulverized anhydrous potassium carbonate was introduced, over the course of 4 hours, into a gently boiling mixture of 144.2 g (1mol) 1-naphthol, 606 g (3mol) 1,3-dibromopropane and 500 ml anhydrous butan-2-one. The reaction mixture was subsequently maintained at the reflux temperature for 4 hours. After cooling, the reaction mixture was filtered with suction and the filter cake washed with acetone.

The combined organic phases were evaporated in a vacuum and the evaporation residue was taken up in chloroform. The chloroform phase was washed several times with dilute aqueous sodium hydroxide solution and then with water and finally dried over anhydrous sodium sulfate. After evaporation of the chloroform, there was obtained a dark oil which was fractionally distilled. 203.3 g (77% of theory) of colorless 1-(naphth-1-yloxy)-3-bromopropane distilled over at 145° – 147° C./0.05 mm.Hg.; $n_D^{20}$= 1.6172.

10.6 g (40 mMol) 1-(naphth-1-yloxy)-3-bromopropane were mixed with 7.7 g (40 mMol) 1-(4-methoxyphenyl)-piperazine, 8.1 g (80 mMol) anhydrous triethylamine and 40 ml. anhydrous tetrahydrofuran and the reaction mixture subsequently maintained at reflux temperature for 10 hours. After cooling, the precipitated triethylamine hydrobromide was filtered off with suction. The filtrate was substantially evaporated in a vaccum, the residue was taken up in chloroform and the solution obtained was shaken with dilute aqueous sodium hydroxide solution, then with an aqueous solution of sodium chloride and thereafter with water. The organic phase was dried over anhydrous sodium sulfate, filtered through active charcoal and finally freed from chloroform in a vacuum. The oily residue was brought to crystallization by the addition of isopropanol. After recrystallization from methanol, with the addition of active charcoal, there were obtained 10.2 g (68% of theory) 1-(4-methoxyphenyl)-4-[3-(naphth-1-yloxy)-propyl]-piperazine, which had a melting point of 68° – 69° C. The corresponding hydrochloride was obtained by passing dry hydrogen chloride through a dioxan solution of the base. It had a melting point of 235° – 238° C.

The compounds of the invention constitute potent anti-hypertensive agents. The compounds have proved particularly effective in the treatment of patients with severe or sustained elevation of blood pressure, particularly diastolic pressure. The compounds are suitable for use in almost all forms of fixed and progressive hypertensive disease, including that in which blood pressure is moderately elevated. The compounds have also proved effective in renal hypertension, including hypertension secondary to pyelonephritis, glomerulonephritis and renal amyloidosis.

The compounds can be administered orally, as pills, tablets, capsules, powders and the like. The preferred form of oral administration is as a tablet containing 1 to 20 mg of active compound.

The compounds can also be administered parenterally. Injection solution containing 10 mg/ml of injection solution are preferred.

The dosage schedule is entirely dependent on the condition of the patient, his response to the treatment and whether or not he is ambulatory or hospitalized. The treatment should be begun with small doses (1mg) and increased gradually depending upon the patient's response. The dosage can be increased at 5 to 7 day intervals until an average daily dose of 1 to 20 mg is reached. Only one dose a day is usually required.

In order to establish the effectiveness of the new compounds of the invention as agents for reducing blood pressure, a series of tests as follows were carried out.

The following were the test methods used:

The test animals were beagles of both sexes into which polyethylene catheters had been implanted in the arteria and vena femoralis. The operation was effected under sterile conditions and under pentobarbital [5-ethyl-5-(1-methylbutyl)barbituric acid]. Meticulous care of the animals and prophylactic administration of antibiotics avoided post-operative complications, so that after a few days the animals were available for the experiments in clinically healthy condition and with the correct physiological characteristics.

During the course of the tests the blood pressure of the dogs was measured via the arterial catheter as well as by an electromechanical pressure transformer (Bell & Howell, 4/327/L 221) and continuously registered on a cable code direct printer (Company Schwarzer, Physiograph). The animals were lying on a table during the tests and were not influenced by any drugs other than the test preparations.

Before the application of the test substance, blood pressure was determined for at least 30 minutes. Then the test compounds were injected via the venous catheter within a time period of 1 minute in a volume of 0.2 ml/kg at a dosage of test compound of 2.5 mg/kg of body weight. The change in the blood pressure 60 minutes after administration of the test substance, relative to the initial value, was measured as a criterion of effectiveness.

Each substance was tested on 4 to 6 dogs and the blood pressure depression values set forth in the Table below represent mean values of the individual tests.

TABLE

| Influence on blood pressure (in mm Hg) by intravenous injection of 2.5 mg/kg of various phenylpiperazines | |
|---|---|
| (Change in the initial values 60 minutes after injection of the test compound.) | |
| TEST COMPOUND | ΔP |
| Comparison Compound: | |
| 1-(4-Chlorophenyl)-4-[3-naphth-1-yl-oxy)-propyl]-piperazine* (described in Chim. Therap. 1966, p. 289) | −14 |
| Inventive Compounds: | |
| 1-Phenyl-4-[3-(naphth-1-yl-oxy)-propyl]-piperazine | − 8 |
| 1-(2-Methoxyphenyl)-4-[3-(naphth-1-yl-oxo)propyl]-piperazine | −18 |
| 1-(4-Methoxyphenyl)-4-[3-(naphth-1-yl-oxy)-propyl]-piperazine | −11 |

*After the application of this substance incompatibility symptoms appeared in form of dyspnea, restlessness and repeated vomiting.

The data in the above table show that the inventive compounds were in part more effacious than the comparison compound in lowering blood pressure while not inducing the undesirable side effects of the comparison material.

For the preparation of pharmaceutical compositions, at least one of the new compounds according to the present invention is mixed with a solid or liquid pharmaceutical diluent or carrier and optionally also with an odoriferous, flavoring and/or coloring material and formed, for example, into tablets or dragees or, with the addition of appropriate adjuvants, suspended or dissolved in an oil, for example olive oil.

It will be understood that the specification and examples are illustrative but not limitative of the present invention and that other embodiments within the spirit and scope of the invention will suggest themselves to those skilled in the art.

What is claimed is:

1. 1-[3-(naphth-1-yloxy)-propyl]-piperazine compound of the formula:

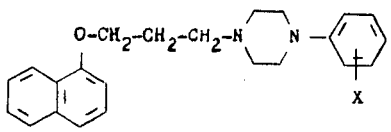 (I)

wherein
X is hydrogen or methoxy;
and the pharmacologically compatible salts thereof.

2. 1-[3-(naphth-1-yloxy)-propyl]-piperazine compound as claimed in claim 1, wherein X is hydrogen.

3. 1-[3-(naphth-1-yloxy)-propyl]-piperazine compound as claimed in claim 1, wherein X is methoxy.

4. 1-[3-(naphth-1-yloxy)-propyl]-piperazine compound as claimed in claim 1, designated 1-phenyl-4-[3-(naphth-1-yloxy)-propyl]-piperazine.

5. 1-[3-(naphth-1-yloxy)-propyl]-piperazine compound as claimed in claim 1, designated 1-(2-methoxyphenyl)-4-[3-(naphth-1-yloxy)-propyl]-piperazine.

6. 1-[3-(naphth-1-yloxy)-propyl]-piperazine compound as claimed in claim 1, designated 1-(4-methoxyphenyl)-4-[3-(naphth-1-yloxy)-propyl]-piperazine.

7. Therapeutic composition for lowering blood pressure comprising pharmaceutically acceptable carrier and as an active ingredient, in an amount effective to lower blood pressure, a 1-[3-(naphth-1-yloxy)-propyl]-piperazine compound as claimed in claim 1.

8. Method of combating hypertension in a subject which method comprises administering to such subject effective amounts of a 1-[3-(naphth-1-yloxy)-propyl]-piperazine compound of the formula:

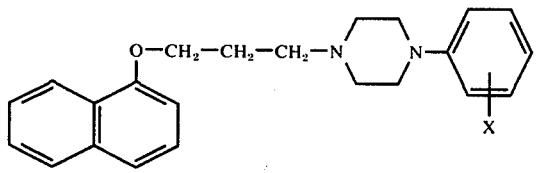 (I)

wherein
X is hydrogen or methoxy;
and the pharmacologically compatible salts thereof.

9. Method as claimed in claim 8 wherein said compound is applied at a dosage of 1 to 20 mg per 75 kg of body weight of the subject.

* * * * *